(12) United States Patent
Trezza, II et al.

(10) Patent No.: US 8,337,415 B2
(45) Date of Patent: Dec. 25, 2012

(54) TISSUE HARVESTING, MINCING, AND TRANSPORT DEVICE

(75) Inventors: Michael J. Trezza, II, Great Meadows, NJ (US); John A. Hibner, Mason, OH (US); Joseph C. Hueil, Loveland, OH (US); Patrick A. Mescher, Bellbrook, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 320 days.

(21) Appl. No.: 12/709,738

(22) Filed: Feb. 22, 2010

(65) Prior Publication Data

US 2011/0208087 A1 Aug. 25, 2011

(51) Int. Cl.
*A61B 10/00* (2006.01)
(52) U.S. Cl. .................................. 600/567; 606/80
(58) Field of Classification Search .............. 600/567; 606/80

See application file for complete search history.

(56) References Cited

U.S. PATENT DOCUMENTS

| | | | |
|---|---|---|---|
| 4,603,694 A | 8/1986 | Wheeler | |
| 4,844,064 A | 7/1989 | Thimsen et al. | |
| 5,649,547 A | 7/1997 | Ritchart et al. | |
| 5,669,876 A | 9/1997 | Schechter et al. | |
| 5,685,840 A | 11/1997 | Schechter et al. | |
| 5,694,951 A | 12/1997 | Bonutti | |
| 6,156,049 A * | 12/2000 | Lovato et al. | 606/170 |
| 6,652,532 B2 | 11/2003 | Bonutti | |
| 6,990,982 B1 | 1/2006 | Bonutti | |
| 7,115,100 B2 | 10/2006 | McRury et al. | |
| 7,226,459 B2 | 6/2007 | Cesarini et al. | |
| 7,481,817 B2 | 1/2009 | Sauer | |
| 7,611,473 B2 | 11/2009 | Boock et al. | |
| 2004/0078090 A1 | 4/2004 | Binette et al. | |
| 2004/0193071 A1 | 9/2004 | Binette et al. | |
| 2005/0038520 A1 | 2/2005 | Binette et al. | |
| 2005/0113736 A1 | 5/2005 | Orr et al. | |
| 2005/0125077 A1 | 6/2005 | Harmon et al. | |
| 2007/0213630 A1 * | 9/2007 | Beckman et al. | 600/562 |
| 2007/0237067 A9 * | 10/2007 | Borran et al. | 370/208 |
| 2008/0071385 A1 | 3/2008 | Binette et al. | |
| 2008/0114264 A1 * | 5/2008 | Weikel et al. | 600/564 |
| 2008/0234715 A1 | 9/2008 | Pesce et al. | |
| 2008/0311219 A1 | 12/2008 | Gosiewska et al. | |

* cited by examiner

*Primary Examiner* — Max Hindenburg
*Assistant Examiner* — Renee Danega
(74) *Attorney, Agent, or Firm* — Frost Brown Todd LLC

(57) ABSTRACT

A device comprises a needle, probe, holster, and tissue collection chamber. A motor simultaneously powers a vacuum pump, translates and rotates a cutter, and translates a plunger. The needle includes a piercing tip and an interior shelf that divides the needle into a cutter lumen and lateral lumen. The cutter and shelf include apertures configured to mince a portion of a tissue specimen that has been severed by the cutter and forced through the apertures by compressive force from the plunger as well as vacuum force. The apertures of the shelf and the apertures of the rotating cutter cooperate to shear the tissue being compressed by the plunger. The minced tissue is then transported to the tissue collection chamber under vacuum force with the assistance of a fluid flush. Collected minced tissue may then be further processed as desired for a given medical treatment or procedure.

9 Claims, 12 Drawing Sheets

TISSUE HARVESTING, MINCING, AND TRANSPORT DEVICE

BACKGROUND

Promoting and improving tissue healing is an important aspect of some medical treatments and procedures. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting and preparing biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
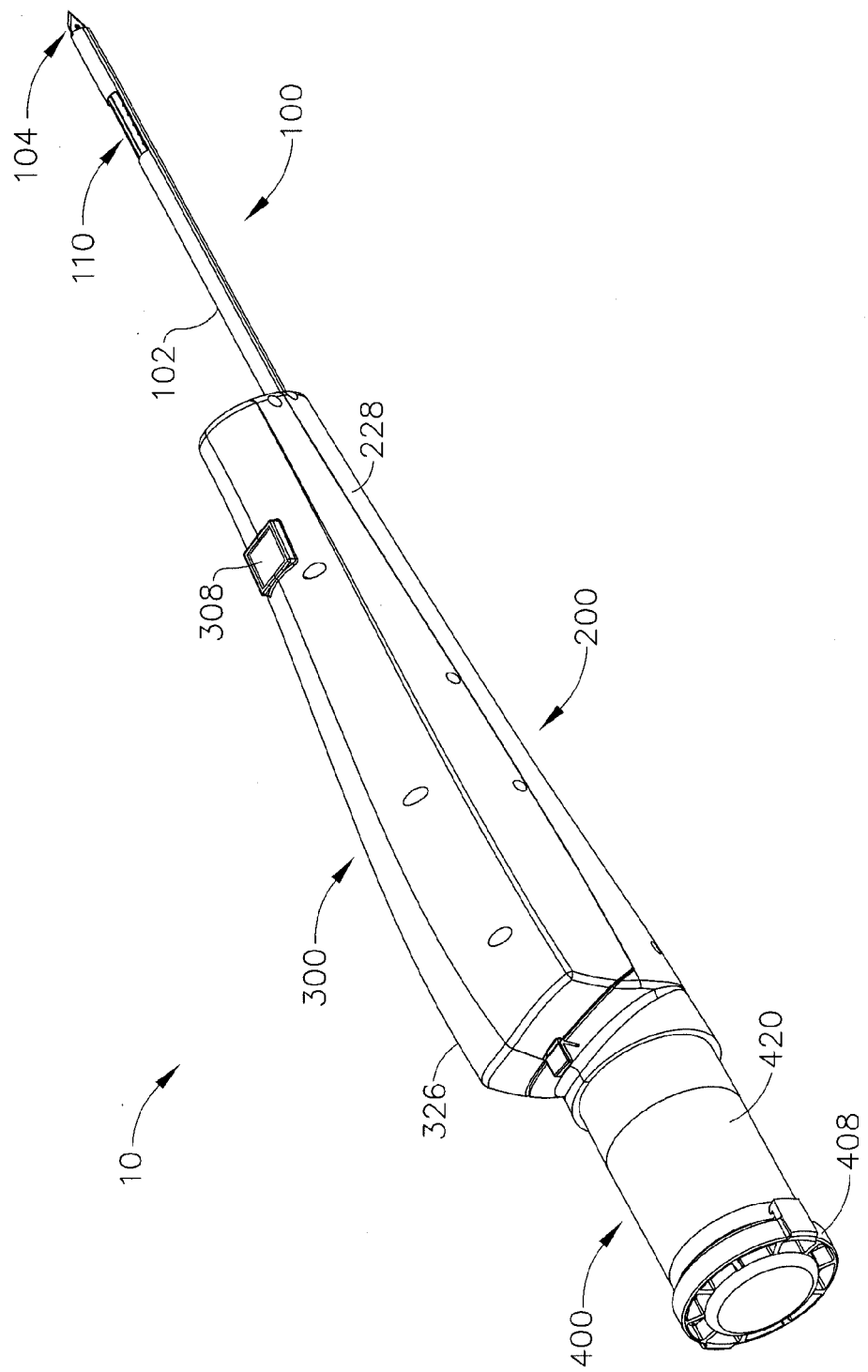
FIG. 1 is a perspective view of an exemplary tissue harvesting and preparation device having a holster, probe, tissue collection chamber, and needle.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

Referring to FIGS. 1-8E, an exemplary device (10) is shown that may be used to harvest tissue from a tissue specimen site, prepare tissue for subsequent use in a medical treatment or procedure, and transport tissue from the site to a tissue collection chamber. Throughout this specification, it should be appreciated that, at times, the term "prepare," in all its forms, may be used to describe not only preparing tissue specimens by mincing, as described further below, but also transporting minced tissue specimens to a tissue collection chamber or elsewhere. Of course it should be appreciated that, at other times, these acts may be described using different terms, or there may be instances where the term "prepare," in all its forms, may only refer to the act of mincing.

Figure 2:
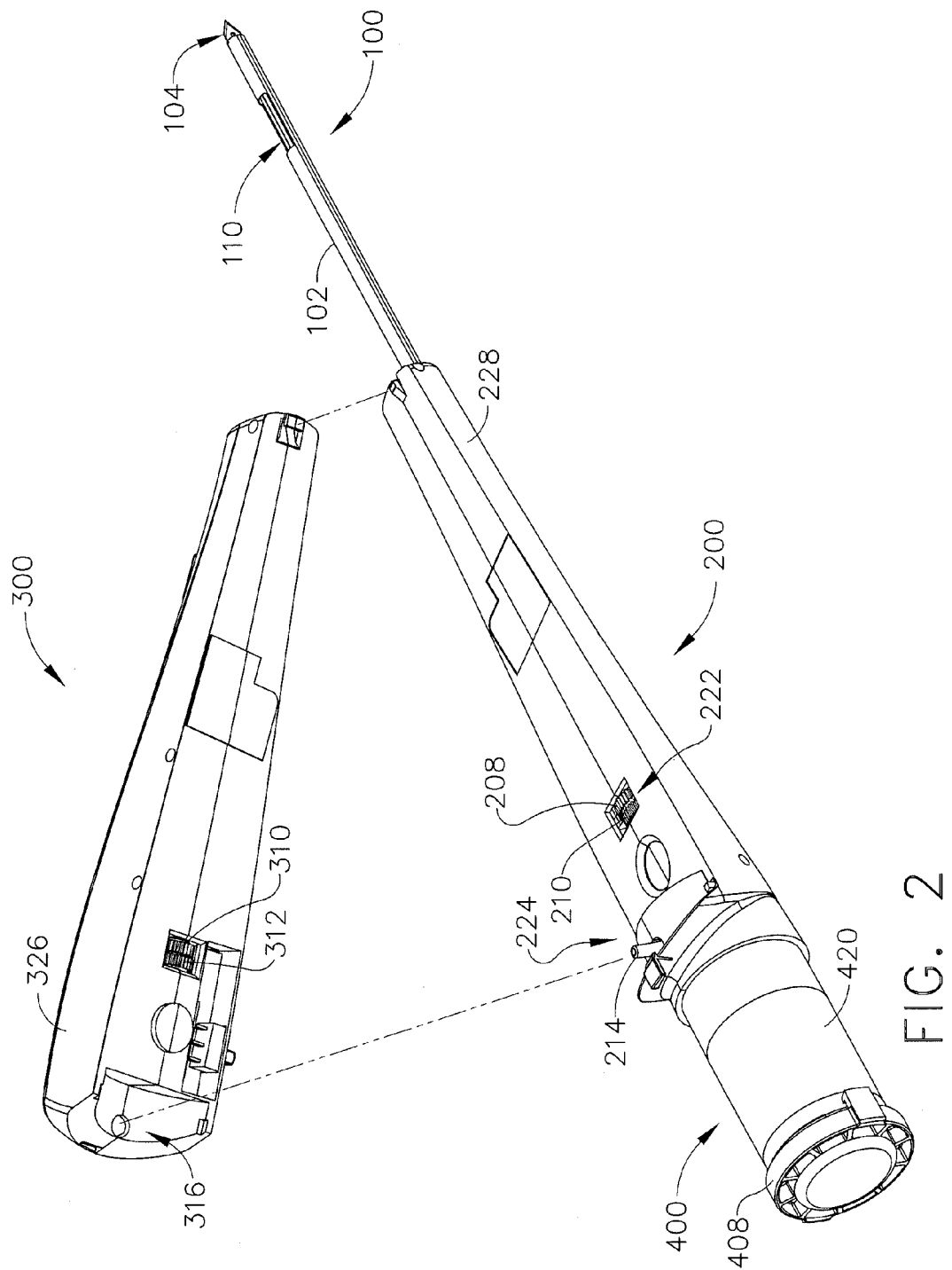
FIG. 2 is a perspective view of the tissue harvesting and preparation device of FIG. 1, with the probe and holster separated from each other.

As shown in FIGS. 1 and 2, device (10) of the present example includes a needle (100), probe (200), holster (300), and tissue collection chamber (400). Each of these components may include additional components and exemplary versions of these components will be described in greater detail below.

I. Exemplary Needle

Referring to FIGS. 1, 2, and 6-8E, an exemplary needle (100), or portions of an exemplary needle (100) are shown. Needle (100) of this example comprises cannula (102), piercing tip (104), cutter (106), and plunger (108). Cannula (102) is a tube-like structure and includes a side aperture (110) within the sidewall of cannula (102). Cannula (102), in conjunction with other features of needle (100) as described below, defines cutter lumen (112), within which cutter (106) is positioned. Within cutter lumen (112), cutter (106) may translate and rotate as described further below. Cannula (102), in conjunction with other features of needle (100) as described below, also defines lateral lumen (114). A manifold (101) is secured to the proximal end of cannula (102) in the present example. Manifold (101) includes a lumen (103) that is in fluid communication with lateral lumen (114) of cannula (102). As will be described in greater detail below, lumen (103) of manifold (101) provides fluid communication from lateral lumen (114) of cannula (102) to a transport tube (226).

Piercing tip (104) of the present example includes a shelf (116) that extends from the proximal area of piercing tip (104) proximally within the space defined by cannula (102). Shelf (116), in combination with cannula (102), defines two lumens within cannula (102) as mentioned above. First, an upper portion of cannula (102) and shelf (116) define cutter lumen (112). Second, a lower portion of cannula (102) and shelf (116) define lateral lumen (114). In the present example, lateral lumen (114) provides a space within which to provide vacuum to the distal end of needle (100); and within which to permit transport of fluids and tissue specimens as will be described further below. A tissue stop (105) extends proximally into cutter lumen (112). While tissue stop (105) is angled such that it faces downwardly, it should be understood that tissue stop (105) may alternatively have any other suitable configuration. It should also be understood that, as with various other components described herein, tissue stop (105) may simply be omitted if desired.

Shelf (116) includes a plurality of apertures (118) near the distal portion of shelf (116). Some apertures (118) are configured such that they are located directly under side aperture (110) of cannula (102). Other apertures (118) are configured such that they are located distal from side aperture (110) of cannula (102). Apertures (118) create an access path to lateral lumen (114) from the interior of cutter (106) via apertures (120) of cutter (106) as described further below. It will be appreciated by those of ordinary skill in the art, based on the teachings herein, that shelf (116) is not required to be a component of piercing tip (104), and may be provided as a separate component of device (10) or as a portion of another component of device (10). For instance, in some other versions, shelf (116) may be coextruded with the remainder of cannula (102), molded as a unitary component of cannula (102), or formed using a variety of other components or techniques. Other suitable structures, features, and configurations for cannula (102) will be apparent to those of ordinary skill in the art in view of the teachings herein.

Figure 7:
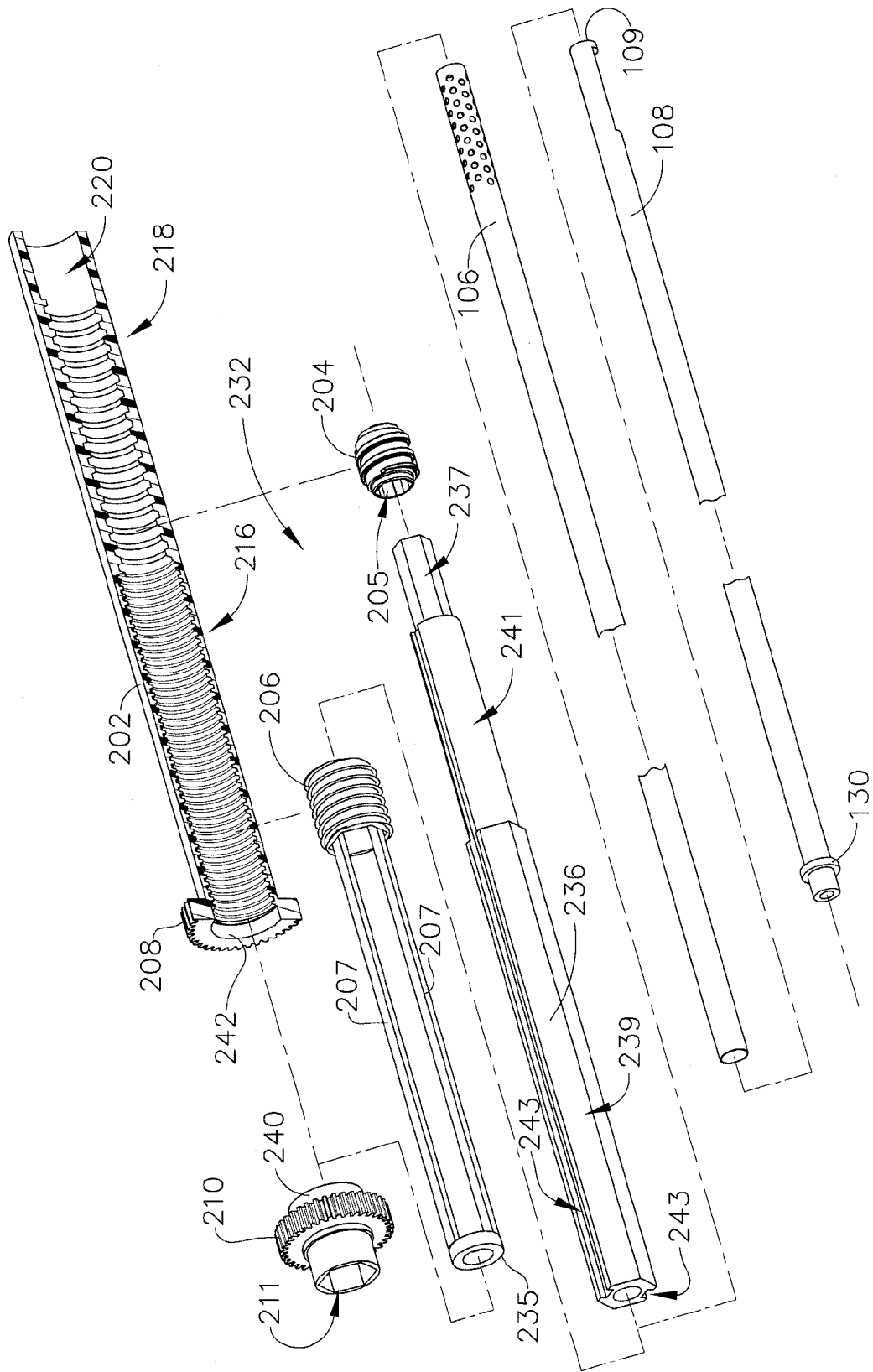
FIG. 7 is an exploded view of cutter and plunger actuation components of the tissue harvesting and preparation device of FIG. 1.
Figure 8A:
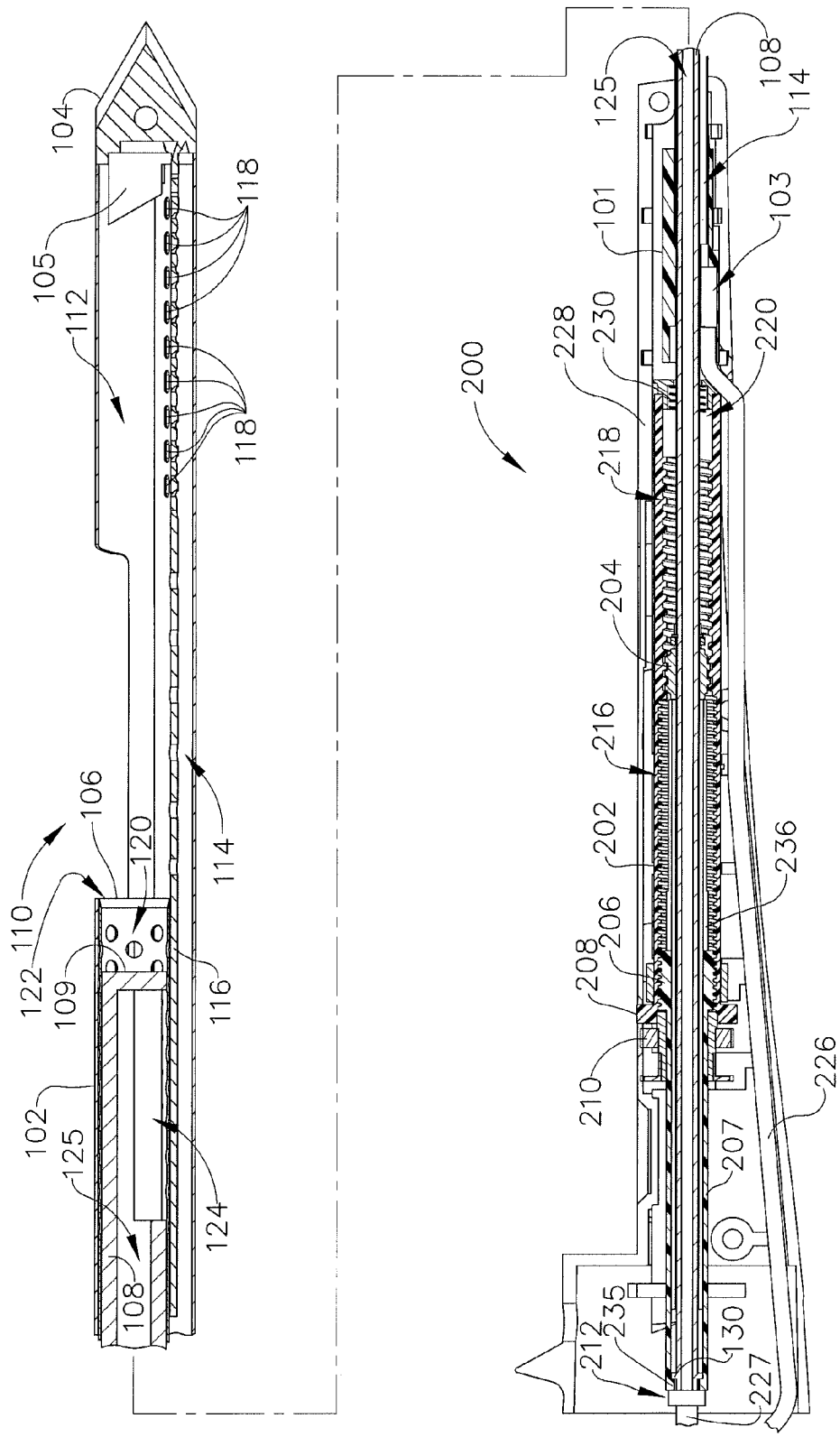
FIG. 8A depicts a side cross-sectional view of cutter and plunger actuation components of the tissue harvesting and preparation device of FIG. 1, with the cutter and plunger each in a proximal-most position.
Figure 8B:
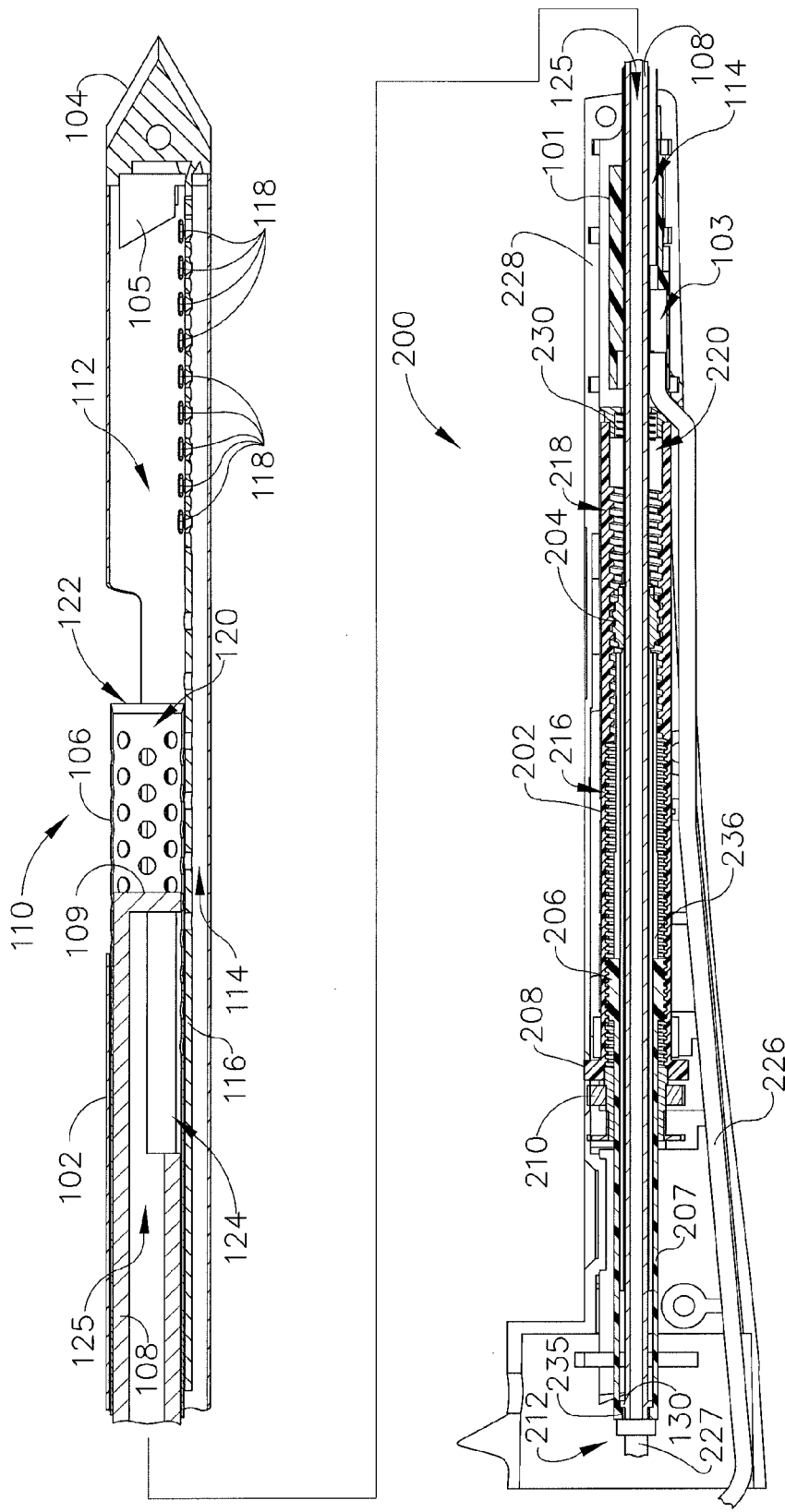
FIG. 8B depicts a side cross-sectional view of the cutter and plunger actuation components of FIG. 8A, with the cutter and the plunger each in a first stage of distal translation.
Figure 8C:
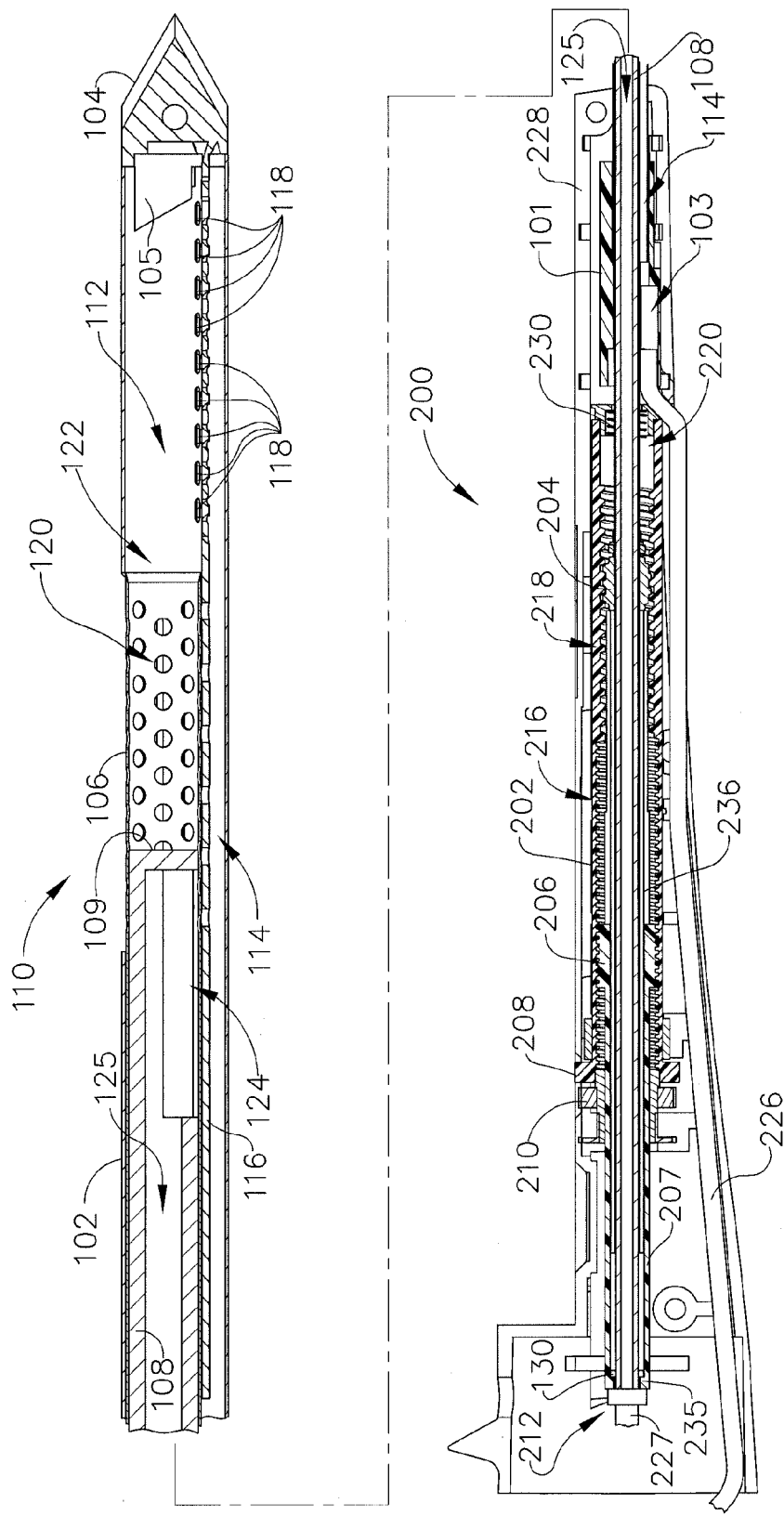
FIG. 8C depicts a side cross-sectional view of the cutter and plunger actuation components of FIG. 8A, with the cutter and the plunger each in a second stage of distal translation.
Figure 8D:
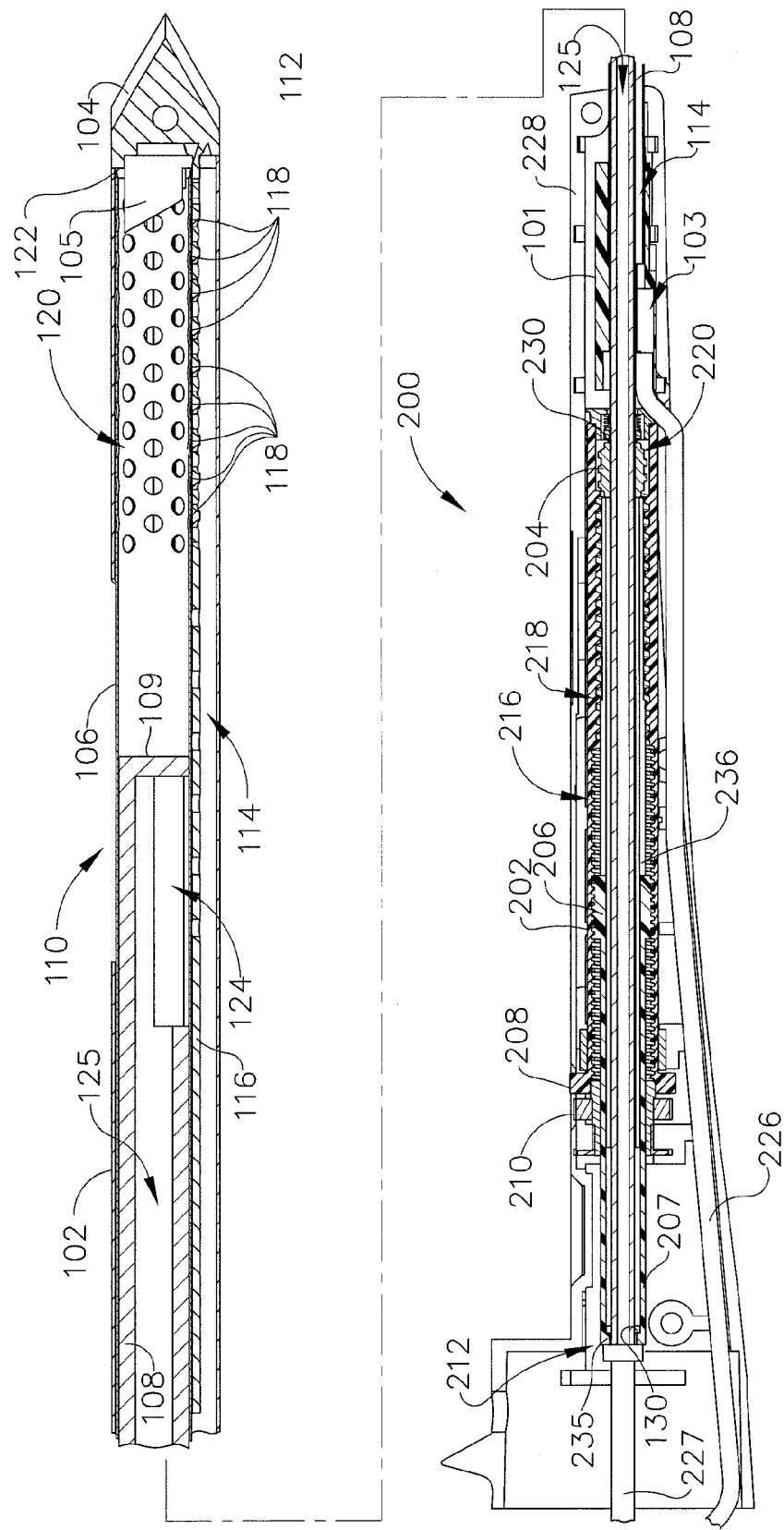
FIG. 8D depicts a side cross-sectional view of the cutter and plunger actuation components of FIG. 8A, with the cutter in a distal-most position and with the plunger continuing to translate distally.
Figure 8E:
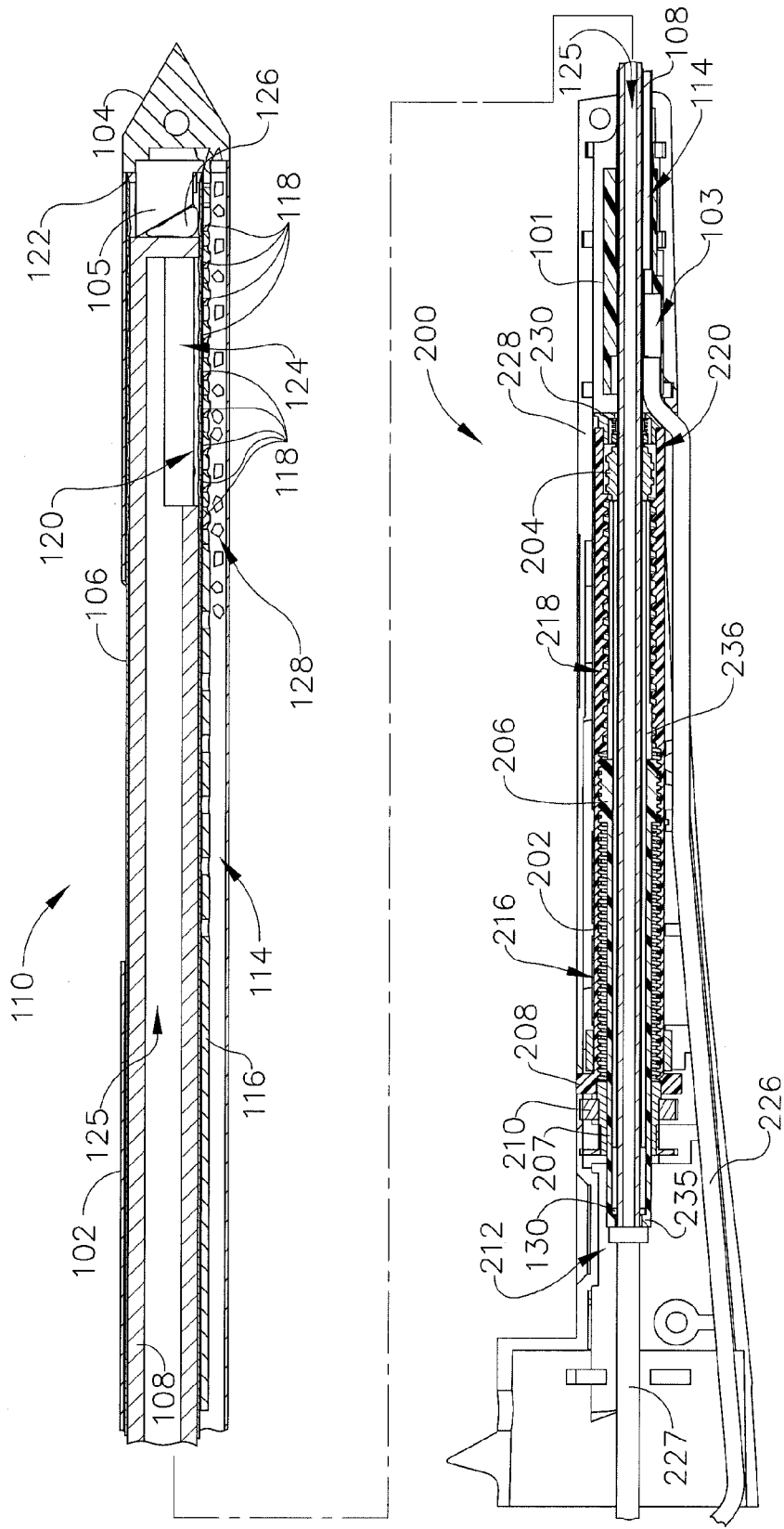
FIG. 8E depicts a side cross-sectional view of the cutter and plunger actuation components of FIG. 8A, with the cutter and the plunger each in a distal-most position.

Cutter (106) of the present example comprises a tube-like structure as shown in FIGS. 7-8E and includes a sharpened distal end (122) that is operable to cut a tissue specimen received within cutter lumen (112) via side aperture (110) of cannula (102) as described further below. Cutter (106) may be operably configured to translate, or even translate and rotate, within cutter lumen (112) as described further below. Cutter (106) of the present example includes a plurality of apertures (120) in the sidewall of cutter (106) near the distal end of cutter (106) as mentioned above. Apertures (120) are configured such that upon full distal advancement of cutter (106) within cutter lumen (112), apertures (120) are located distal of side aperture (110) of cannula (102). Of course other arrangements for apertures (120) may be used as well. Apertures (120) are configured to work with other features of needle (100), as described further below, to prepare a tissue specimen captured within cutter lumen (112) and severed by cutter (106). As shown in FIG. 8D, tissue stop (105) is dimensioned to be received within cutter (106) when cutter (106) reaches a distal-most position. Other suitable structures, features, and configurations for cutter (106) will be apparent to those of ordinary skill in the art in view of the teachings herein.

Plunger (108) of the present example is positioned within cutter (106), as shown in FIGS. 7-8E. Plunger (108) may be operably configured to translate, or even translate and rotate, within cutter (106) as described further below. Plunger (108) comprises a tube-like structure include opening (124) in its sidewall near the distal end and a longitudinal lumen (125) in communication with opening (124). A saline tube (227) is coupled with the proximal end of plunger (108) at a fluid fitting (212), and is in fluid communication with lumen (125) of plunger (108). Saline tube (227) is also coupled with a source (not shown) of fluid such as saline. Of course, any other suitable fluids may be used, including but not limited to various liquids, pressurized air, atmospheric air, etc. Opening (124) is configured to provide communication of fluid from saline tube (227), through lumen (125) of plunger (108), out opening (124), and into lateral lumen (114). For instance, as seen in FIG. 8E, when plunger (108) is advanced to a distalmost position, opening (124) is positioned above apertures (120) of cutter (106) and apertures (118) of shelf (116). In this configuration, fluid from saline tube (227) may be transmitted through lumen (125) of plunger (108), out opening (124), then through apertures (120) and apertures (118) into lateral lumen (114). While plunger (108) has been described as a hollow, tube-like structure, plunger (108) may alternatively be a solid structure, not operably configured to transmit fluid therethrough and into lateral lumen (114). Other suitable structures, features, and configurations for plunger (108) will be apparent to those of ordinary skill in the art in view of the teachings herein.

II. Exemplary Probe

Figure 5:
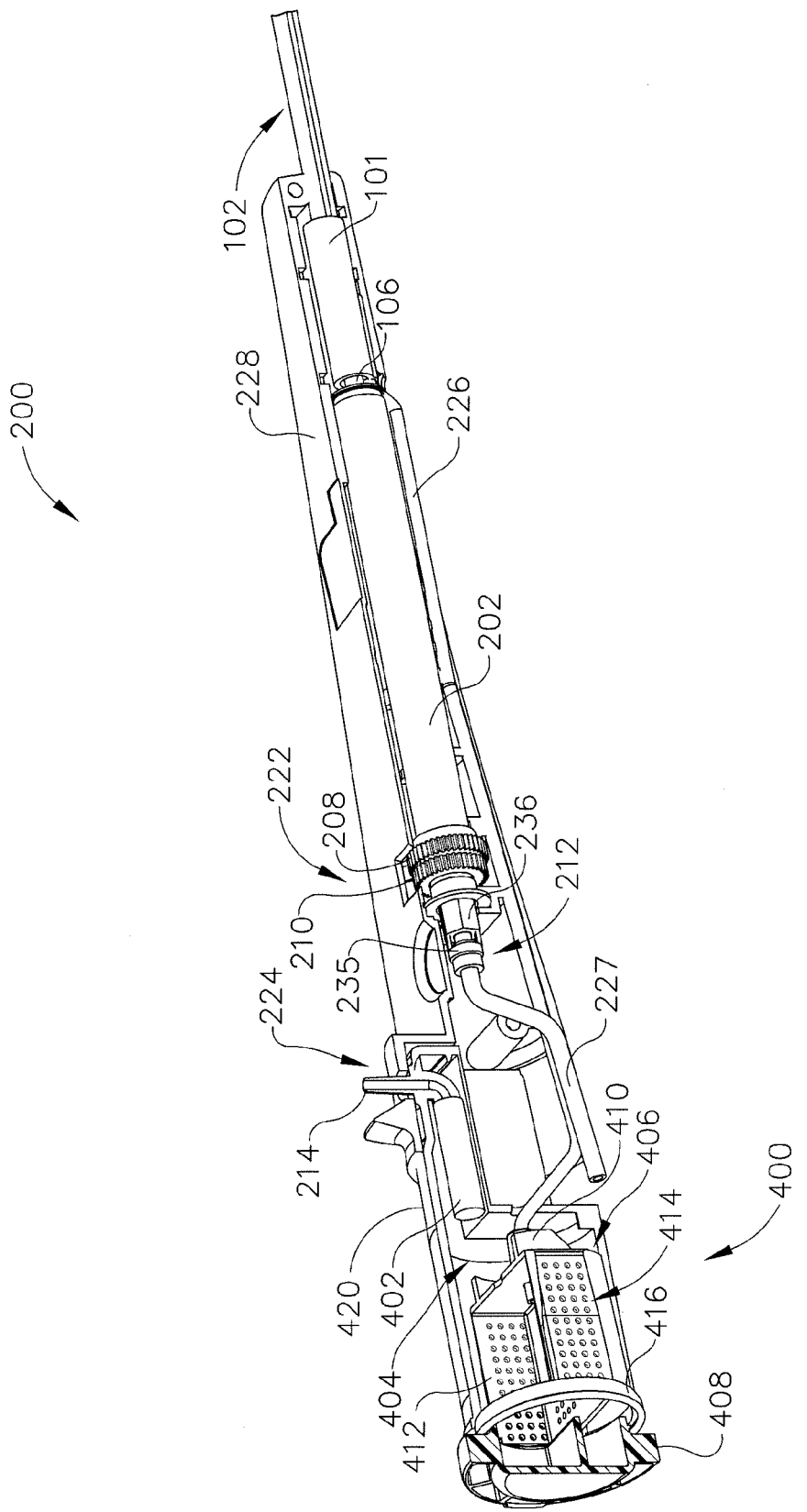
FIG. 5 is a perspective view of the probe and tissue collection chamber of the tissue harvesting and preparation device of FIG. 1, shown with the probe housing and tissue collection chamber housing in cross section.

Referring to FIGS. 1-3 and 5-8E, probe (200) of the present example includes housing (228), lead screw (202), cutter nut (204), plunger nut (206), translation gear (208), rotation gear (210), fluid fitting (212), vacuum fitting (214), transport tube (226), and cutter overmold (236). As shown in FIGS. 2 and 5, gears (208, 210) are partially exposed through window (222) in housing (228) in the present example, and are configured to mesh with gears (310, 312) of holster (300) when probe (200) and holster (300) are coupled together. In particular, and as will be described in greater detail below, holster (300) is operable to rotatingly drive gears (310, 312), which rotate gears (208, 210), which in turn simultaneously provide rotation and translation of cutter (106) as well as translation of plunger (108).

Cutter overmold (236) is secured unitarily to the exterior of the proximal portion of cutter (106). In particular, cutter overmold (236) is formed of plastic that is overmolded about metal cutter (106). Of course, cutter overmold (236) may be formed of any other suitable material or combination of materials and/or may be secured to cutter (106) using any other suitable technique or combination of techniques. With cutter overmold (236) being secured unitarily to cutter (106) in the present example, cutter overmold (236) and cutter (106) rotate and translate unitarily. As will be described in greater detail below, such rotation and translation is provided by rotation of translation gear (208) and rotation gear (210).

As best seen in FIG. 7, cutter overmold (236) includes a distal set of exterior flats (237), a proximal set of exterior flats (239), and a smooth exterior portion (241) positioned longitudinally between flats (237, 239). An opposing pair of recesses (243) extend longitudinally along proximal exterior flats (239) and longitudinally along smooth exterior portion (241). Of course, this configuration of cutter overmold (236) is merely on example. Various other suitable configurations for cutter overmold (236) will be apparent to those of ordinary skill in the art in view of the teachings herein.

Cutter nut (204) is positioned about distal exterior flats (237). In particular, cutter nut (204) includes a plurality of interior flats (205) that complement distal exterior flats (237). Thus, cutter nut (204) rotates unitarily with cutter overmold (236) (and, hence, cutter (106)) in the present example. In addition, cutter nut (204) is slidably disposed about distal exterior flats (237). A distal coil spring (230) is positioned about cutter overmold (236), distal to cutter nut (204). An "e-clip" (not shown) is also positioned about cutter overmold (236), distal to distal coil spring (230), such that distal coil spring (230) is longitudinally positioned between cutter nut (204) and the e-clip. Thus, the e-clip and distal coil spring (230) cooperate to resiliently bias cutter nut (204) proximally. In addition, cooperation of cutter nut (204), cutter overmold (236), distal coil spring (230), and the e-clip provide translation of cutter (106) upon sufficient translation of cutter nut (204) (e.g., such that distal spring (230) is fully compressed); with translation of cutter nut (204) being provided through interaction between threading of cutter nut (204) and coarse pitch threaded portion (218) as cutter nut (204) is rotated relative to lead screw (202). In some versions, a proximal coil spring is also positioned about cutter overmold (236), proximal to cutter nut (204) and distal to smooth exterior portion (241) of cutter overmold (236). In still other versions, cutter nut (204) is secured unitarily to cutter overmold (236), such that cutter nut (204) translates unitarily with cutter overmold (236) (and, hence, cutter (106)). In some such versions, distal coil spring (230) is still positioned about cutter overmold (236), to bias cutter nut (204) proximally when cutter nut (204) reaches free-wheeling portion (220) of lead screw (202) as described below. Of course, cutter nut (204) and the distal portion of cutter overmold (236) may have any other suitable features, configurations, and relationships.

Plunger nut (206) is positioned about proximal exterior flats (239). As best seen in FIG. 7, a pair of arms (207) extend proximally from plunger nut (206). In the present example, arms (207) are unitarily secured to plunger nut (206), such that arms (207) rotate and translate unitarily with plunger nut (206). For instance, plunger nut (206) and arms (207) may be molded together as a single piece. Alternatively, plunger nut (206) and arms (207) may be formed in any other suitable fashion. Arms (207) are received in longitudinal recesses (243) of cutter overmold (236) in the present example. With arms (207) being received in longitudinal recesses (243), arms (207) and plunger nut (206) rotate unitarily with cutter overmold (236). However, neither arms (207) nor plunger nut (206) are fixed to cutter overmold (236). Thus, arms (207) and plunger nut (206) are allowed to translate relative to cutter overmold (236).

Arms (207) proximally terminate in a ring (235). Ring (235) is positioned about the proximal end of plunger (108). In particular, ring (235) abuts the proximal face of flange (130) in the present example Accordingly, and as will be described in greater detail below, as plunger nut (206), arms (205), and ring (235) translate distally, ring (235) pushes plunger (108) distally. In addition, as plunger nut (206), arms (205), and ring (235) translate proximally, ring (235) pushes plunger (108) proximally by pushing against fitting (212), which is rigidly secured to plunger (108) in the present example. Accordingly, it should be understood that plunger nut (206), arms (205), ring (235), and plunger (108) all translate unitarily in distal and proximal directions in the present example. However, ring (235) is not fixed to plunger (108). Thus, ring (235) is allowed to rotate relative to plunger (108). In other words, rotation of plunger nut (206), arms (205), and ring (235) does not cause corresponding rotation of plunger (108) in the present example. In some other versions, ring (235) is fixed to plunger (108), such that rotation of plunger nut (206) does cause corresponding rotation of plunger (108). Various suitable alternative configurations of and relationships between plunger nut (206) and plunger (108) will be apparent to those of ordinary skill in the art in view of the teachings herein.

Rotation gear (210) is also positioned about proximal exterior flats (239). Rotation gear (210) includes a plurality of interior flats (211) that complement proximal exterior flats (239). Thus, rotation gear (210) rotates unitarily with cutter overmold (236). As noted above, cutter nut (204) and cutter (106) also rotate unitarily with cutter overmold (236); as do plunger nut (206) and arms (207). Accordingly, rotation of rotation gear (210) drives rotation of cutter (106) in the present example. While rotation gear (210) rotates unitarily with cutter overmold (236) in the present example, rotation gear (210) is not fixed to cutter overmold (236). Thus, cutter overmold (236) is permitted to translate relative to rotation gear (210). It should be understood that cutter overmold (236) and rotation gear (210) may include a variety of other features (e.g., in lieu of complementary flats (239, 211)) to provide rotation of cutter (106) by rotation of rotation gear (210), including but not limited to complementary teeth or splines, a complementary key and keyway, etc. It should also be understood that cutter (106) and rotation gear (210) may be in communication via a variety of alternative intermediary components, including but not limited to one or more gears or elongate members with splines.

Plunger nut (206) and arms (207) are also permitted to translate relative to rotation gear (210) in the present example, with arms (207) being positioned within interior flats (211) of rotation gear (210) through a longitudinal range of travel of plunger nut (206) relative to rotation gear (210). In particular, longitudinal recesses (243) and arms (207) are dimensioned such that the combination of arms (207) and cutter overmold (236) are permitted to translate relative to and within rotation gear (210). As will be described in greater detail below, rotation of rotation gear (210) provides simultaneous rotation and translation of cutter (106) as well as translation of plunger (108).

Translation gear (208) is integrally formed at the proximal end of lead screw (202) in the present example. For instance, translation gear (208) and lead screw (202) may be molded as a single unitary component. Alternatively, any other suitable techniques may be used to form and/or join translation gear (208) and lead screw (202). Rotation gear (210) includes a hub portion (240) that fits within a recessed portion (242) of translation gear (208), providing support to translation gear (208) and lead screw (202). Rotation gear (210) is nevertheless rotatable relative to translation gear (208). In the present example, lead screw (202) rotates unitarily with translation gear (208), yet lead screw (202) does not translate relative to housing (228). Lead screw (202) is in communication with cutter nut (204) and plunger nut (206) via interior threads along a portion of its length. In particular, lead screw (202) of the present example includes fine pitch threaded portion (216) near its proximal end and coarse pitch threaded portion (218) near its distal end. Lead screw (202) also includes a non-threaded free-wheeling portion (220) distal of coarse pitch threaded portion (218). Optionally, lead screw (202) may also include similar free-wheeling portions located between coarse threaded portion (218) and fine threaded portion (216), or at a proximal end of lead screw (202).

Cutter nut (204) includes threads configured to engage the coarse threads of lead screw (202). As shown in FIGS. 8A-8C, cutter nut (204) is positioned along the coarse pitch threaded portion (218) of lead screw (202) during a range of longitudinal travel of cutter nut (204), such that the threads of cutter nut (204) engage with the threads of coarse pitch threaded portion (218) of lead screw (202). As noted above, cutter nut (204) is further associated with cutter (106). With such a configuration, and as will also be described in greater detail below, rotation of cutter nut (204) relative to lead screw (202) causes cutter nut (204) and cutter (106) to translate. When cutter nut (204) translates to a distal-most position, cutter nut (204) encounters free-wheeling portion (220) of lead screw (202). Upon encountering free-wheeling portion (220), cutter nut (204) (and, hence, cutter (106)) ceases further distal translation despite continued rotation of cutter nut (204) relative to lead screw (202). This configuration may provide desirable operational features with respect to the operability of cutter (106) and plunger (108) as will be described in greater detail below. Furthermore, in some versions including an optional free-wheeling portion between coarse threaded portion (218) and fine threaded portion (216), cutter nut (204) may free-wheel upon full retraction of cutter nut (204) along fine threaded portion (216) of lead screw (202).

As shown in FIGS. 8A-8E, coil spring (230) is associated with free-wheeling portion (220) such that cutter nut (204) is proximally biased to re-engage coarse pitch threaded portion (218) of lead screw (202) upon a reversal in translational direction that may be attributed to a reversal in rotational direction of cutter nut (204) relative to lead screw (202). With such rotation being reversed, and with cutter nut (204) being re-engaged with coarse pitch threaded portion (218) of lead screw (202), cutter nut (204) will move cutter (106) proximally as cutter nut (204) translates proximally. Of course, any other suitable type of resilient member may be used in addition to or in lieu of coil spring (230). It should also be understood that, when the rotational direction is reversed to retract cutter nut (204) and cutter (106) proximally, such reversal in the rotational direction will also cause plunger nut (206) to retract proximally. With ring (235) of plunger nut (206) bearing against fitting (212), and with fitting (212) being rigidly secured to plunger (108), such retraction of plunger nut (206) will provide corresponding proximal retraction of plunger (108) in the present example.

Cutter nut (204) may be associated with lead screw (202) and cutter (106) in a variety of ways. In the present example, lead screw (202), cutter nut (204), and cutter (106) are all aligned along a common longitudinal axis. As shown in FIGS. 7-8E, lead screw (202) includes an interior passageway within which cutter nut (204) and cutter (106) may translate. This configuration may be used when lead screw (202) has an interior threaded portion, or partially threaded interior portion, while cutter nut (204) has complementary exterior threads for engaging coarse pitch threaded portion (218) of lead screw (202), as described above.

In some other versions, lead screw (202) is configured with external threads while cutter nut (204) is configured with internal threads for engaging coarse pitch threaded portion (218) of lead screw (202). With such a configuration, cutter nut (204) may be positioned around the outer portion of lead screw (202). Furthermore, lead screw (202) and cutter nut (204) may have a common longitudinal axis, but one that may be offset from, and may be parallel with, a longitudinal axis of cutter (106). Cutter nut (204) may also be configured with one or more pushing members that may engage one or more portions of cutter (106) to translate cutter (106) in response to translation of cutter nut (204) that may be caused by rotation of cutter nut (204) relative to lead screw (202). Other suitable configurations of and relationships between cutter nut (204)

and/or lead screw (202) will be apparent to those of ordinary skill in the art in view of the teachings herein.

Similar to cutter nut (204), plunger nut (206) of the present example includes threads configured to engage threads of lead screw (202). As shown in FIGS. 7-8E, plunger nut (206) is positioned along the fine pitch threaded portion (216) of lead screw (202) throughout a range of travel of plunger nut (206), such that the threads of plunger nut (206) engage with the fine pitch threaded portion (216) of lead screw (202). As noted above, plunger nut (206) is further associated with the proximal end of plunger (108). With such a configuration, and as will also be described in greater detail below, rotation of plunger nut (206) relative to lead screw (202) causes plunger nut (206) and plunger (108) to translate. In versions including free wheeling portions distal of and/or proximal of fine pitch threaded portion (216) of lead screw (202), plunger nut (206) may encounter free-wheeling portions upon either full distal translation or full proximal translation such that plunger nut (206) may cease further translation despite continued rotation of plunger nut (206) relative to lead screw (202).

Plunger nut (206) may be associated with lead screw (202) and plunger (108) in a variety of ways. In the present example, lead screw (202), plunger nut (206), and plunger (108) are all aligned along a common longitudinal axis. As shown in FIGS. 7-8E, lead screw (202) includes an interior passageway within which plunger nut (206) and plunger (108) may translate. This configuration may be used when lead screw (202) has an interior threaded portion, or partially threaded interior portion, while plunger nut (206) has complementary exterior threads for engaging fine pitch threaded portion (216) of lead screw (202), as described above.

In some other versions, lead screw (202) may be configured with external threads while plunger nut (206) is configured with internal threads for engaging fine pitch threaded portion (216) of lead screw (202). With such a configuration, plunger nut (206) may be positioned around the outer portion of lead screw (202). Furthermore, lead screw (202) and plunger nut (206) may have a common longitudinal axis, but one that may be offset from, and may be parallel with, a longitudinal axis of plunger (108). Plunger nut (206) may also be configured with one or more pushing members that may engage one or more portions of plunger (108) to translate plunger (108) in response to translation of plunger nut (206) that may be caused by rotation of plunger nut (206) relative to lead screw (202). Other suitable configurations of and relationships between plunger nut (206) and/or lead screw (202) will be apparent to those of ordinary skill in the art in view of the teachings herein.

As shown in FIGS. 7-8E, the configuration of lead screw (202), cutter nut (204), and plunger nut (206) is such that the length of lead screw (202) and its respective threaded portions (216, 218), combined with the position of cutter nut (204) and plunger nut (206), allows for a staged operability of cutter (106) and plunger (108). For instance, the length of lead screw (202) and the lengths of its threaded portions (216, 218) is such that when cutter nut (204) reaches free-wheeling portion (220), plunger nut (206) is engaged with fine pitch threaded portion (216). Thus, lead screw (202) and plunger nut (206) are still be operable to provide translational energy to plunger (108) despite cutter (106) translating no further distally.

Also, the difference in the pitch of threaded portions (216, 218) of lead screw (202) provide for cutter nut (204) and plunger nut (206) to achieve different translational velocities. For instance, plunger nut (206) will have a slower translation velocity moving along the fine pitch threaded portion (216) compared to that of the cutter nut (204) moving along the coarse pitch threaded portion (218). In other words, while both cutter (106) and plunger (108) translate relative to lead screw (202), cutter (106) and plunger (108) translate at different rates, with cutter (106) translating faster than plunger (108). For instance, cutter nut (204) and cutter (106) translate a greater distance than plunger nut (206) and plunger (108) over the same time span since cutter nut (204) is associated with coarse pitch threaded portion (218) of lead screw (202), while plunger nut (206) is associated with fine pitch threaded portion (216). Since cutter overmold (236) translates unitarily with cutter (106), and since plunger nut (206), arms (207), and ring (235) translate distally with plunger (108), and further since plunger nut (206) and arms (207) are slidable relative to cutter overmold (236), cutter overmold (236) translates distally relative to plunger nut (206) and arms (207) as cutter (106) and plunger (108) are being distally translated simultaneously. It should also be understood that a finer pitch for threaded portion (216) may provide increased mechanical advantage to plunger (108) as it translates. This operability of cutter (106) and plunger (108) will be described in greater detail below.

In the present example, and as noted above, gears (208, 210) are rotated simultaneously during operation of device (10). In particular, gears (208, 210) are rotated simultaneously in the same direction in the present example. Thus, cutter overmold (236), cutter nut (204), plunger nut (208), and lead screw (202) all rotate simultaneously and in the same direction during operation of device (10). However, gears (208, 210) have different pitch diameters in the present example, such that gears (208, 210) will rotate simultaneously at different speeds. Accordingly, in the present example, cutter overmold (236), cutter nut (204), and plunger nut (208) will all rotate based on one rotational speed; while lead screw (202) will simultaneously rotate at a different rotational speed. So even though cutter nut (204) and lead screw (202) rotate simultaneously in the same direction, the difference between rotational speeds of cutter nut (204) and lead screw (202) provide a net result of cutter nut (204) rotating relative to lead screw (202). Such relative rotation provides translation of cutter (106) while cutter (106) rotates as described above. Similarly, even though plunger nut (206) and lead screw (202) rotate simultaneously in the same direction, the difference between rotational speeds of plunger nut (206) and lead screw (202) provide a net result of plunger nut (206) rotating relative to lead screw (202). Such relative rotation provides translation of plunger (108) as described above.

In some other versions, lead screw (202) simply stays stationary relative to housing (228) and does not rotate at all. In such versions, rotation of cutter nut (204) and plunger nut (206) is still relative to lead screw (202), which will still provide translation of cutter (106) and plunger (108). It should therefore be understood that translation gear (208) is merely optional. In some other versions, rotation gear (210) is rotated in a direction opposite to the direction of rotation of translation gear (208). It should also be understood that there are a variety of other ways to associate lead screw (202), cutter nut (204), plunger nut (206), cutter (106), plunger (108), translation gear (208), and rotation gear (210) to achieve translation and rotation of cutter (106), while also achieving translation of plunger (108), and at the same time controlling translation such that cutter (106) and plunger (108) translate at different rates. Other suitable components, features, variations, operabilities, and relationships between these components will be apparent to those of ordinary skill in the art in view of the teachings herein.

Based on the teachings herein, those of ordinary skill in the art will appreciate that the configuration of fluid fitting (212)

at the proximal end of plunger (108) is such that saline tube (227) and plunger (108) remain in communication throughout the translation cycle of plunger (108). For example, fluid fitting (212) may be securely connected to the proximal end of plunger (108) and saline tube (227) may be of sufficient length to still extend outside of probe (200) for connection to a fluid source while saline tube (227) is being pulled further into probe (200) during an advancement stroke of plunger (108). In other words, as plunger (108) translates, fluid fitting (212) and saline tube (227) may move with plunger (108) within probe (200) and remain in communication with both plunger (108) and the fluid source. As another merely illustrative example, the proximal end of plunger (108) may extend within and translate within a fluid manifold. Saline tube (227) may be coupled with such a manifold, such that the manifold communicates fluid from saline tube (227) to lumen (125) of plunger (108). A seal may be maintained between the exterior of plunger (108) and such a manifold. The manifold may remain stationary within probe (200) during translation of plunger (108), such that saline tube (227) also stays stationary relative to probe (200) during translation of plunger (108). Other suitable ways in which communication between plunger (108) and a fluid source may be maintained during and through the translation range of plunger (108) will be apparent to those of ordinary skill in the art in view of the teachings herein.

Figure 3:
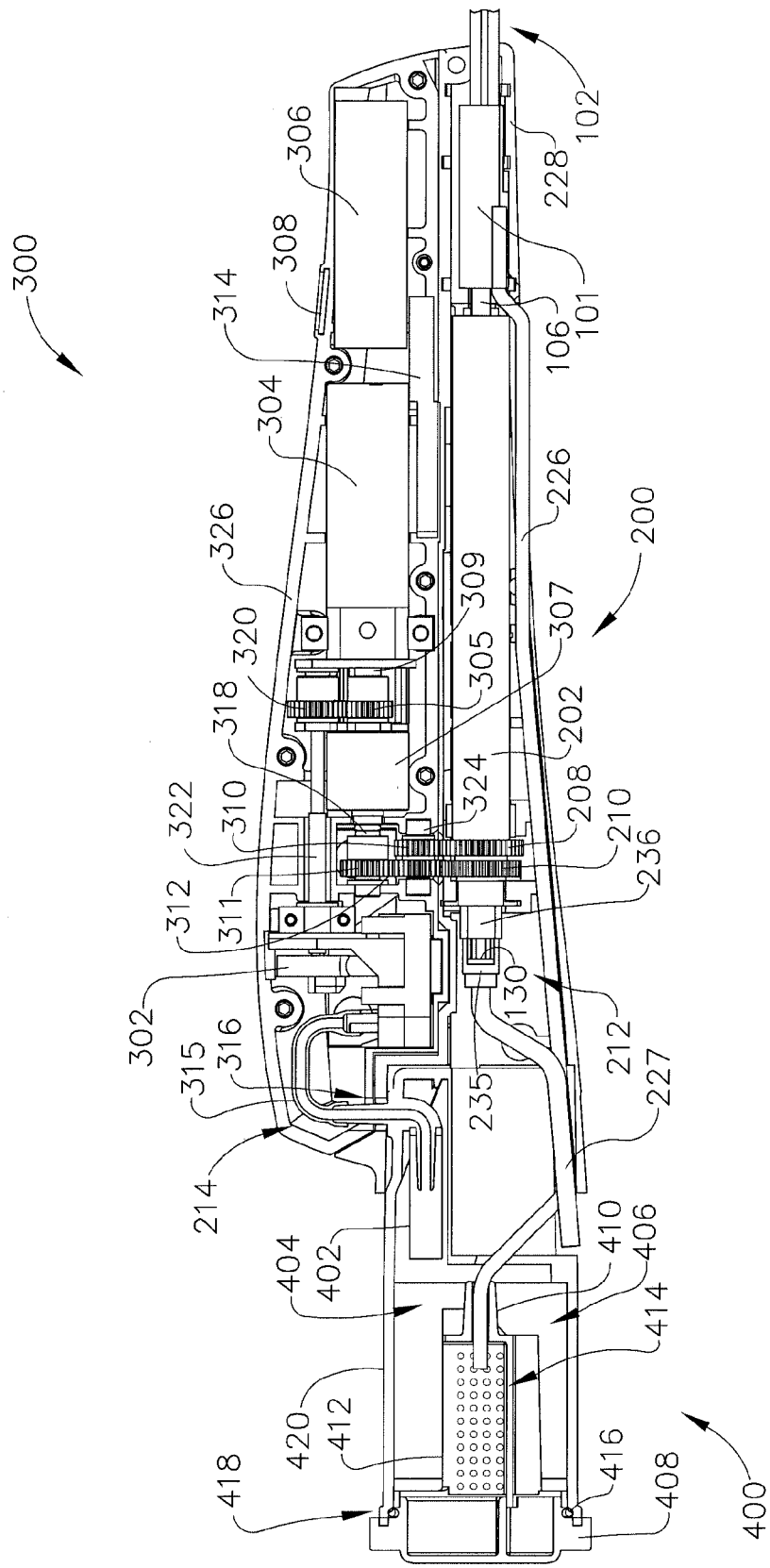
FIG. 3 is a side view of the probe, holster, and tissue collection chamber portions of the tissue harvesting and preparation device of FIG. 1, with holster housing, probe housing, and tissue collection chamber housing components in cross section.

As shown in FIGS. 2-3 and 5, a vacuum fitting (214) is provided near the proximal end of probe (200) in the present example Probe (200) includes an opening (224), through which vacuum fitting (214) may pass for connecting with other components. In particular, as shown in FIG. 3, vacuum fitting (214) is configured to be in communication with vacuum pump (302) of holster (300) at one end. At the other end, vacuum fitting (214) is in communication with tissue collection chamber (400) as will be described further below. In some other versions, device (10) is configured such that vacuum fitting (214) connects to a vacuum source completely external to device (10). Furthermore, it will be appreciated, based on the teachings herein, that vacuum fitting (214) may be a component of holster (300) or tissue collection chamber (400) instead of probe (200).

Probe (200) of the present example also includes transport tube (226), which is in fluid communication with lateral lumen (114) of needle (100) at the distal end of transport tube (226). In particular, and as described above, the distal end of transport tube (226) is coupled with lateral lumen (114) of needle (100) via manifold (101). As will be discussed further below, the proximal end of transport tube (226) is in communication with tissue collection chamber (400). In such a configuration, transport tube (226) permits minced tissue particles to be transported from lateral lumen (114) to tissue collection basket (406) using vacuum and optional fluid assistance, as will be discussed further below. In some versions, transport tube (226) may be a component of tissue collection chamber (400), or some other component of device (10), instead of probe (200). It should also be understood that probe (200) and transport tube (226) may include windows and/or transparent portions such that transport tube (226) may be viewable to a user to confirm tissue particle capture and transport. In addition, other suitable features, components, configurations, and operabilities that may be provided by probe (200) will be apparent to those of ordinary skill in the art in view of the teachings herein.

III. Exemplary Holster

Figure 4:
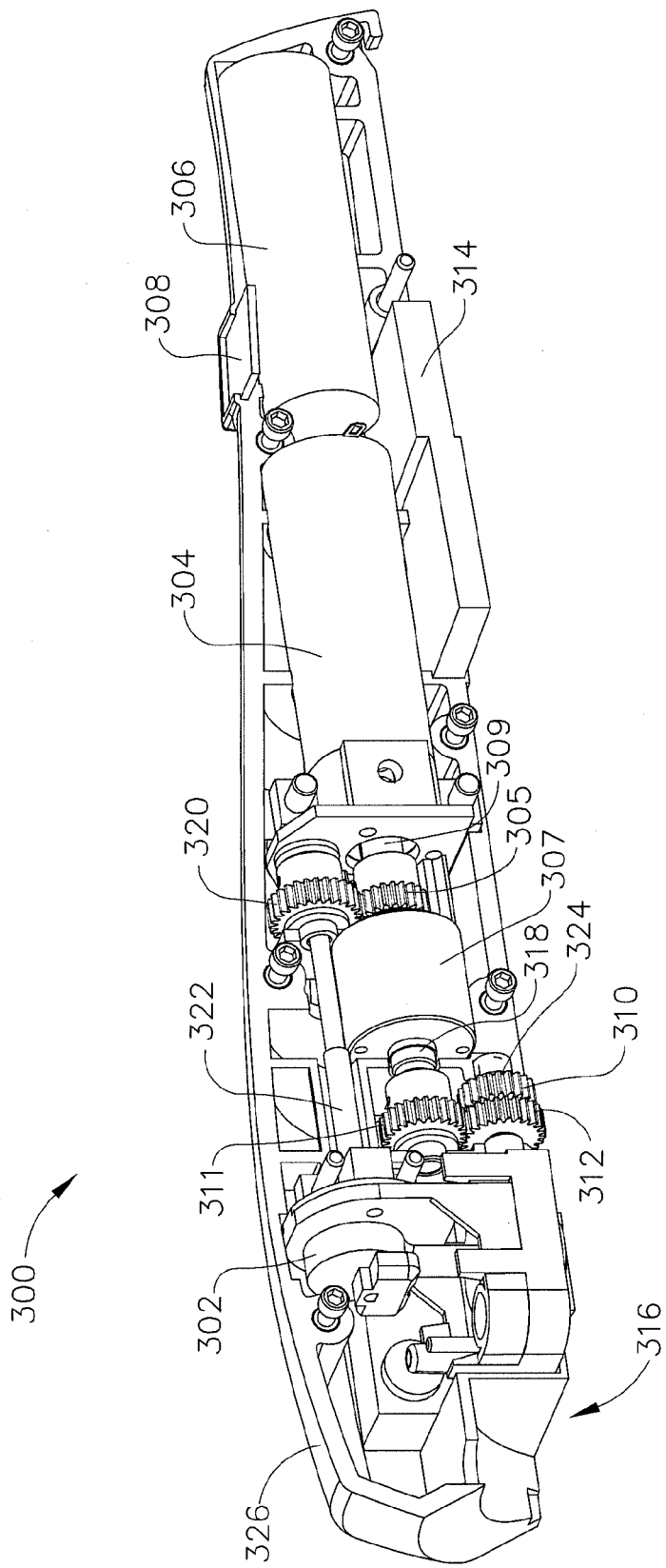
FIG. 4 is a perspective view of the holster of the tissue harvesting and preparation device of FIG. 1, shown with the holster housing in cross section to expose components of the drive system for the cutter and plunger as well as components of the vacuum system.

Referring to FIGS. 2-4, holster (300) of the present example includes housing (326), vacuum pump (302), motor (304), battery (306), actuation button (308), translation drive gear (310), rotation drive gear (312), and printed circuit boards (314). Probe (200) and holster (300) are removably coupled together in the present example. For instance, probe (200) may be provided as a disposable component, while holster (300) may be provided as a reusable component after sterilization. As noted above, gears (310, 312) are configured to mesh with gears (208, 210) when probe (200) is coupled with holster (300). Furthermore, and as will be described in greater detail below, motor (304) is operable to drive gears (208, 210), which will in turn drive gears (208, 210) to provide simultaneous rotation and translation of cutter (106) as well as translation of plunger (108). As seen in FIGS. 2-5, gears (310, 312) are positioned within holster (300) such that a portion of each gear (310, 312) protrudes from holster (300), thereby permitting gears (310, 312) to mesh with gears (208, 210). To locate gear (310, 312) with portions protruding from holster (300), the rotational axis of gears (310, 312) is offset from drive shaft (318) of motor (304). With such an offset configuration, one or more intermediate gears may be used to communicate rotational energy from drive shaft (309) of motor (304) to gears (310, 312) as described in greater detail below. While probe (200) and holster (300) are provided as separable components in the present example, it should be understood that holster (300) and probe (200) may alternatively be configured as a single unitary component.

Vacuum pump (302) is operable to generate a vacuum and communicate the vacuum to vacuum fitting (214) as described above. In particular, and as shown in FIGS. 2-4, holster (300) includes a port (316) that is configured to receive vacuum fitting (214) of probe (200) when probe (200) and holster (300) are joined as shown in FIGS. 1 and 3. A tube (315) joins vacuum fitting (214) with vacuum pump (302) in the present example, though it should be understood that vacuum pump (302) may be coupled with vacuum fitting (214) in any other suitable fashion. In the present example, vacuum pump (302) is powered by motor (304) as will be described in greater detail below. Of course vacuum pump (302) may, instead or in addition, be powered by a motor or other structure located remote from device (10). As another merely illustrative example, device (10) may receive vacuum from a remote source, such that vacuum pump (302) may be omitted. For instance, vacuum fitting (214) or some other feature of device (10) may be tethered to a remote vacuum source via a tube or other type of conduit, etc.

Motor (304) is powered by battery (306) in the present example. Alternatively, motor (304) may be powered by some external power source remote from device (10). For instance, motor (304) may be coupled with a power cable or cord leading to an external power source, etc. A drive shaft (309) extends from motor (304), and motor (304) is operable to rotate drive shaft (309) in at least one direction. A driving gear (305) is positioned about drive shaft (309), such that rotation of drive shaft (309) rotates driving gear (305). Driving gear (305) meshes with driven gear (320), which is secured to a second shaft (322). Second shaft (322) is in communication with vacuum pump (302), such that rotation of second shaft (322) causes vacuum pump (302) to generate a vacuum. Vacuum pump (302) of the present example comprises a conventional diaphragm pump. In particular, a second shaft (322) is coupled with an eccentric disk (not shown—e.g., a device for converting circular motion into rectilinear motion, comprising a disk fixed off-center to second shaft (322)), which is configured to cause a rod (not shown—e.g., the rod may be coupled with or otherwise driven by the eccentric disk) of vacuum pump (302) to reciprocate as motor (304) and shafts (309, 322) rotate. This rod of vacuum pump (302) drives a diaphragm (not shown) of vacuum pump (302) as the rod reciprocates, causing vacuum pump (302) to induce a vacuum. It should be understood that vacuum pump (302) of the present example operates in the same way regardless of which direction motor (302) rotates. Of course, any other suitable type of vacuum source may be used.

In the present example, drive shaft (309) of motor (304) also extends into a gearbox (307), providing a driving input into gearbox (307). A third shaft (318) extends from gearbox (307), providing a driven output from gearbox (307). A gear (311) is secured to third shaft (318). Gear box (307) houses a plurality of gears (not shown) that are configured to provide a rotational speed differential such that gear (311) rotates at a different speed compared to gear (305). In this manner, gear box (307) allows for motor (304) to simultaneously drive multiple components of device (10) at different rotational speeds. Gear (311) meshes with rotation drive gear (312), such that rotation of gear (311) rotates rotation drive gear (312). Rotation drive gear (312) is secured to a fourth shaft (324), such that rotation of rotation drive gear (312) rotates fourth shaft (324). Translation drive gear (310) is also secured to fourth shaft (324), such that rotation of fourth shaft (324) rotates translation drive gear (310). Gears (311, 310, 312) all thus rotate concomitantly. As noted above, rotation of gears (310, 312) causes rotation of gears (208, 210), which in turn causes simultaneous rotation and translation of cutter (106) as well as translation of plunger (108). It should therefore be understood that, with such configurations as described, motor (304) is capable of simultaneously operating vacuum pump (302), rotating and translating cutter (106), and translating plunger (108). Of course device (10) could also be configured such that more than one motor (304) may be used to operate these components.

Battery (306) is positioned within holster (300) and provides power to motor (304) as mentioned above. Battery (306) may be configured such that it is easily replaced when its power expires. In some other versions, battery (306) is configured such that it is rechargeable. In some such versions, device (10), or holster (300) of device (10), may be configured with an electrical input to charge battery (306). Still in other such versions, device (10), or holster (300) of device (10), may be configured with exposed or exposable electrical contacts, where these contacts are configured to work with a powered docking member having electrical contacts for recharging battery (306). Battery (306) may comprise one or more alkaline batteries, one or more nickel-cadmium batteries, one or more lithium-ion batteries, or any other suitable battery type. Still, it will be appreciated based on the teachings herein, that battery (306) may be omitted entirely and instead device (10) may be tethered via an electrical or pneumatic cable to a power source to provide power to motor (304). For instance, motor (304) may include an impeller responsive to pressurized air or some other type of pressurized medium. It should also be understood that cutter (106) and/or plunger (108) may be driven by a pneumatic motor and/or actuator, a hydraulic motor and/or actuator, or a variety of other types of components. Various other suitable driving means, as well as various suitable ways in which such driving means may be incorporated into device (10), will be apparent to those of ordinary skill in the art in view of the teachings herein.

Figure 6:
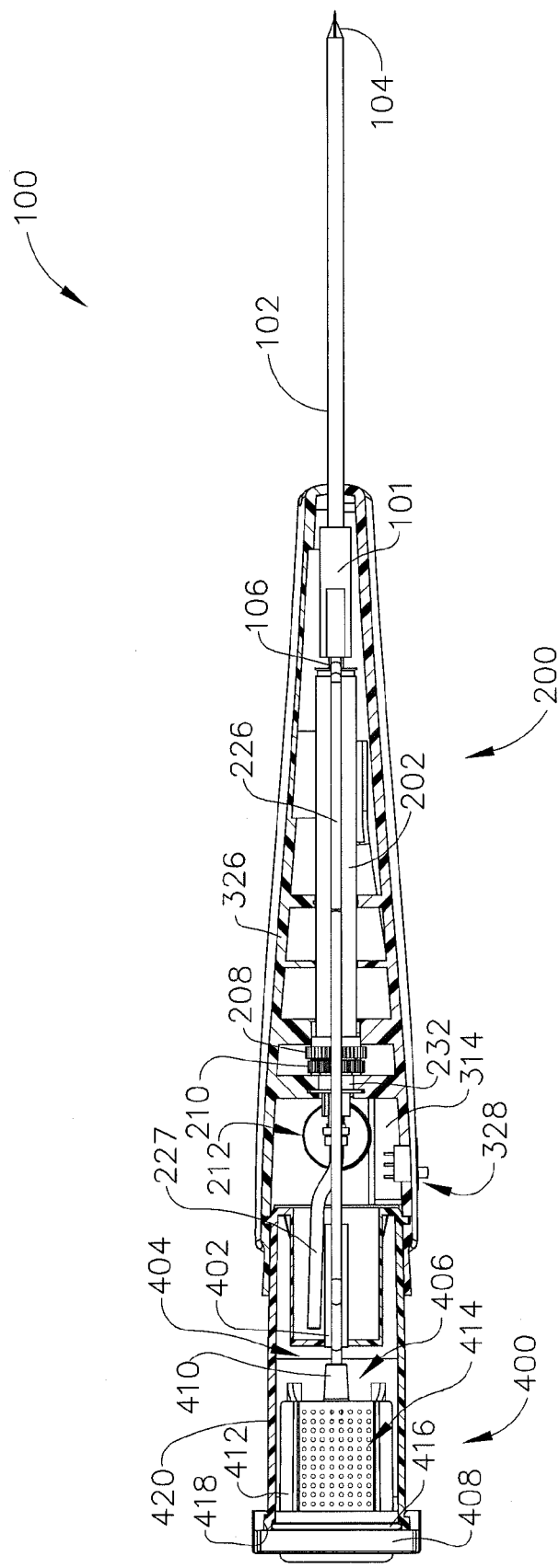
FIG. 6 is a bottom view of the tissue harvesting and preparation device of FIG. 1, shown without the probe housing and with the tissue collection chamber housing in cross section.

Actuation button (308) is in communication with motor (304) via printed circuit boards (314), such that depressing actuation button (308) causes motor (304) to rotate. For instance, actuation button (308), when depressed, may cause power from battery (306) to be sent to motor (304). In response, motor (304) may rotate in either a first or second direction as described further below. As shown in FIG. 6, an on/off switch (328) is provided that must be moved to the "on" position before actuation button (308) will have any effect on device (10) in the present example. Of course, such an on/off switch (328) is merely optional. Actuation button (308) may be mechanically activated by physical depression of button (308). Still in other versions, actuation button (308) may touch-sensitive such that physical depression of button (308) is not required, e.g. using capacitive switching technology, etc. As shown in FIGS. 1, 3, and 4, actuation button (308) of the present example consists of a single button that is configured to control motor (304) rotation in either direction. Still in other versions, more than one actuation button (308) may be included with device (10) to control motor (304). Still yet in other versions, other structures, e.g. switches, may be configured with device (10) to control directional rotation of motor (304), while actuation button (308) may be limited to activate motor (304) to rotate in whatever direction is selected according to the switch or other structure. Other suitable ways in which control of motor (304) and thus operation of device (10) may be provided will be apparent to those of ordinary skill in the art in view of the teachings herein. By way of example only, depressing actuation button (308) a second time may stop or pause motor (304) in some versions. In some other versions, depressing and holding actuation button (308) for an extended period may cancel a harvesting cycle and return the components of device (10) to a "home" position that may include cutter (106) and plunger (108) retracted proximal from side aperture (110).

Printed circuit boards (314) of the present example comprise conventional "off the shelf" components. Printed circuit boards (314) are in communication, directly or indirectly, with on-off switch (328), actuation button (308), battery (306), and motor (304) to electrically connect and control device (10). Based on the teachings herein, it will be appreciated by those of ordinary skill in the art that other types of circuitry, e.g., wire-wrapped or point-to-point constructed circuits among others, may be adapted for use with device (10) in addition to or instead of printed circuit boards (314). In addition, other suitable features, components, configurations, and operabilities that may be provided by holster (300) will be apparent to those of ordinary skill in the art in view of the teachings herein.

IV. Exemplary Tissue Collection Chamber

As shown in FIGS. 1-3, 5, and 6, tissue collection chamber (400) is located at the proximal end of probe (200) of device (10) in the present example. Tissue collection chamber (400) may be entirely detachable from probe (200); or selected components of tissue collection chamber (400) may be detachable from probe (200). Tissue collection chamber (400) includes housing (420), fitting (402), hollow interior (404), tissue collection basket (406), and end cap (408). These components will be described in greater detail below.

Fitting (402) is located within hollow interior (404) and presents an opening that is coupled with one end of vacuum fitting (214) of probe (200). When probe (200) and holster (300) are coupled together, fitting (402) and vacuum fitting (214) are configured to communicate a vacuum from vacuum pump (302) to hollow interior (404) of tissue collection chamber (400). Fitting (402) may include a hydrophobic filter, occluding media, or similar feature configured to prevent fluids from being communicated from hollow interior (404) to vacuum pump (302) when a vacuum is being drawn through fitting (402). Hollow interior (404) is further configured to communicate such a vacuum to transport tube (226), which proximally terminates within hollow interior (404). In some versions, vacuum fitting (214) of probe (200) is combined with fitting (402) to create a single fitting of tissue collection chamber (400). With tissue collection chamber (400) installed at the proximal end of probe (200), this single fitting may pass through opening (224) in probe (200) such that it may engage port (316) of holster (300) to thereby communicate vacuum from vacuum pump (302) (or some other vacuum source) to tissue collection chamber (400).

Tissue collection basket (406) is also located within hollow interior (404), as shown in FIGS. 3, 5, and 6. Tissue collection basket (406) includes a fitting (410) at its distal end. Fitting (410) is coupled with transport tube (226) of probe (200). In some other versions, fitting (410) is omitted entirely and transport tube (226) terminates directly over tissue collection basket (406) or is otherwise engaged with tissue collection basket (406). Tissue collection basket (406) of the present example comprises partially enclosed body (412). Body (412) is configured to receive minced tissue particles communicated proximally through transport tube (226). Body (412) includes a plurality of apertures (414) configured to permit fluids to pass through apertures (414). Apertures (414) may further be configured such that minced tissue particles collected within tissue collection basket (406) do not pass through apertures (414). In some versions, tissue collection basket (406) is formed at least in part by a screen.

End cap (408) is detachably connected to a proximal end of housing (420). End cap (408) is further engaged with tissue collection basket (406) in the present example. With end cap (408) associated with tissue collection basket (406), such detachability may provide an easy way to remove collected tissue particles from tissue collection chamber (400). To ensure that end cap (408) creates a sealed connection with tissue collection chamber (400), an o-ring (416) is located between end cap (408) and the proximal end of tissue collection chamber (400). In the present example, end cap (408) includes a groove (418) for locating o-ring (416). In connecting end cap (408) with housing (420) any suitable connection type may be used. For instance, in some versions, end cap (408) may be configured with a snap-fitting connection with tissue collection chamber (400). Still in other versions, end cap (408) may include a threaded portion and tissue collection chamber may include a corresponding threaded portion such that end cap (408) and tissue collection chamber (400) may connect in a screw-on fashion. Still other suitable ways in which an end cap (408) may be associated with tissue collection chamber (400) will be apparent to those of ordinary skill in the art in view of the teachings herein. In addition, other suitable features, components, configurations, and operabilities that may be provided by tissue collection chamber (400) will be apparent to those of ordinary skill in the art in view of the teachings herein.

V. Exemplary Operation and Use

In use, device (10) is operably configured to sever tissue specimen (126) from a tissue specimen (e.g., within an adult human) and then prepare the tissue specimen by mincing it into smaller particles or pieces (128), as shown in FIG. 8E. Once prepared, the minced pieces (128) may be transported to tissue collection chamber (400) for later collection, processing, and use in a medical treatment or procedure. Device (10) may come from the manufacturer as a ready-to-use unit or it may come in components that may be assembled by a user. Where device (10) comprises a series of components assembled by a user, the components may be connectable by any suitable means. For example, probe (200) and holster (300) may be configured with snap-fitting connections. Similarly, tissue collection chamber (400) may snap-fit with probe (200) or may screw into probe (200) as described above. Needle (100) may be integral with probe (200) or needle (100) may screw into or snap-fit with probe (200). Various suitable ways in which the components of device (10) may be assembled and/or disassembled will be apparent to those of ordinary skill in the art in view of the teachings herein.

Once device (10) is assembled and ready for use, it may be inserted into a patient's tissue to harvest a tissue specimen (126). In an initial position, cutter (106) is advanced distally (126) to close off side aperture (110) of cannula (102). Needle (100) is then inserted into the patient's tissue. By way of example only, needle (100) may be inserted in a patient's thigh muscle or in any other suitable location. After needle (100) is located by the user in a desired position relative to the tissue specimen in the patient, actuation button (308) may be depressed to begin the harvesting of tissue specimen (126) from the patient's tissue. In response to actuation button (308) being depressed, motor (304) begins to rotate gears (310, 312) in a first direction and also rotate second shaft (322) to activate vacuum pump (302). As described above, the rotation of gear (310) ultimately causes cutter (106) to translate within cannula (102). With gear (310) being rotated in the first direction, cutter (106) translates proximally to open side aperture (110) as shown in FIG. 8A. At this stage, plunger (108) is also at a proximal position.

With side aperture (110) open, the vacuum generated by vacuum pump (302) is communicated through vacuum fitting (214) and fitting (402) of tissue collection chamber (400) into hollow interior (404) and ultimately through transport tube (226), manifold (101) and lateral lumen (114) to side aperture (110) via apertures (118). The vacuum delivered to side aperture (110) may be sufficient to cause a portion of the patient's tissue to prolapse through side aperture (110) and into cutter lumen (112).

Once tissue is within cutter lumen (112), upon full retraction of cutter (106), motor (304) may reverse direction, rotating now in a second direction. This direction reversal of motor (304) may cause gears (310, 312) to also rotate in a second direction. Such rotation of gears (310, 312) in the second direction ultimately causes cutter (106) to rotate and translate distally within cannula (102), thereby advancing cutter (106) to close-off side aperture (110) and sever tissue specimen (126) from the patient's tissue. Such rotation of gears (310, 312) in the second direction also causes plunger (108) to translate distally. As shown in FIGS. 8B-8D, plunger (108) trails behind cutter (106) as they both advance distally. During this process, rotation of motor (304) continues to activate vacuum pump (302) to draw a vacuum through lateral lumen (114). As noted above, vacuum pump (302) operates in the same fashion regardless of which direction second shaft (322) is rotated in.

As cutter (106) begins distally traversing side aperture (110), as shown in FIG. 8B, sharpened distal end (122) of cutter (106) begins severing tissue that is prolapsed through side aperture (110). Once distal end (122) of cutter (106) has moved distal to the distal-most edge of side aperture (110), as shown in FIG. 8C, distal end (122) of cutter (106) has completely severed a tissue specimen from the patient's tissue. While not shown in FIG. 8C, it should be understood that this tissue specimen will be located somewhere between tissue stop (105) and the distal face (109) of plunger (108) at this stage.

As cutter (106) reaches a distal-most position, as shown in FIG. 8D, cutter nut (204) reaches free-wheeling portion (220) of lead screw (202), such that cutter (106) ceases further distal translation, yet continues to rotate. In the meantime, plunger (108) continues to advance distally with continued differential rotation of lead screw (202) and cutter overmold (236) and resulting distal movement of plunger nut (206). Distal face (109) of plunger (108) eventually contacts tissue specimen (126) captured within cutter lumen (112) and previously severed by cutter (106). Plunger (108) then pushes tissue specimen (126) against tissue stop (105) and thereby begins to compress tissue specimen (126) in this distal region of needle (100). In the present example, this occurs between the stages of operation depicted in FIGS. 8E-8D. With tissue specimen (126) being compressed between distal face (109) and tissue stop (105), vacuum continues to be applied to the distal end of needle (100) via lateral lumen (114). This combination of compression and vacuum causes portions of tissue specimens (126) to be forced within apertures (120) of cutter (106) and apertures (118) of shelf (116). With rotation of cutter (106), the portions of tissue specimen (126) within apertures (120, 118) are severed from tissue specimen (126), such that tissue specimen (126) is minced. Thus, the combination of plunger (108), tissue stop (105), apertures (120) of rotating cutter (106), and apertures (118) of shelf (116) provide a cutting action on tissue specimen (126) similar to that of a cheese grater. In other words, apertures (120) of rotating cutter (106) and apertures (118) of shelf (116) cooperate to shear tissue specimen (126) into minced pieces (128).

Once the portion of tissue specimen (126) has been minced, minced pieces (128) are drawn into lateral lumen (114) with assistance provided by vacuum in lateral lumen (114). In the present example, saline is communicated through saline tube (227) and through lumen (125) of plunger (108). This saline is further communicated through side opening (124) of plunger (108) and through apertures (120, 118) of cutter (106) and shelf (116). This communication of saline provides a pressure differential sufficient to flush minced pieces (128) proximally through lateral lumen (114), through manifold (101), through transport tube (226), and ultimately into tissue collection basket (406). As noted above, such saline may be at atmospheric pressure or may be pressurized. As also noted above, any other suitable fluid may be used instead of saline, including but not limited to other liquids, pressurized air, atmospheric air, etc. In the present example, apertures (414) of tissue collection basket (406) permit any excess fluid to drain through tissue collection basket (406) and into hollow interior (404) while minced tissue (128) is retained within tissue collection basket (406). Furthermore, tissue collection chamber (400) may be fitted with a drain plug or other type of feature to permit periodic draining of fluid collected within hollow interior (404). As another merely illustrative alternative, a hydrophilic material or other absorbent material may be provided within hollow interior (404) to soak up saline and/or other fluids.

When plunger (108) reaches the distal end of needle (100), the sample cycle may be considered complete. Once complete, the sample cycle may be repeated to gather additional minced tissue (128) if so desired. This may be accomplished by repositioning the already inserted device (10), e.g. by altering the depth and side aperture (110) orientation, such that removal and reinsertion is not required to harvest multiple tissue specimens (126) from a patient. The rotational direction of motor (304) may be reversed to retract cutter (106) and plunger (108) proximally; then reversed again to advance cutter (106) and plunger (108) distally for additional cycles. Once a desired amount of minced tissue (128) has been collected, tissue collection basket (406) may be removed from probe (200) by removing end cap (408). At this point, minced tissue (128) may be further processed as may be desired by a user for subsequent use in a medical treatment or procedure.

It should be understood that the above-described use is merely one example of a way in which device (10) may be used. Various other suitable ways in which device (10) may be used will be apparent to those of ordinary skill in the art in view of the teachings herein.

It should also be understood that, through the use of a clutch or other structure, device (10) may be operably configured such that cutter (106) only rotates upon distal translation and not also proximal translation. Also, based on the teachings herein, those of ordinary skill in the art will appreciate that motor (304) may change rotation automatically upon full retraction of cutter (106) as described, or user controls may be included to permit motor (304) rotation direction to be dictated by the user, e.g. via a directional switch or other suitable features. Furthermore, in some versions of device (10), motor (304) simply rotates only in one direction. For instance, in some such versions, cannula (102) is inserted into tissue with cutter (106) and plunger (108) already in the proximal-most positions; and cutter (106) and plunger (108) are only advanced to the distal-most positions once before cannula (102) is removed from the patient (e.g., within cutter (106) and plunger (108) being retracted within cannula (102) after reaching the distal-most positions).

While several tissue harvesting, mincing, and transport devices, and components thereof, have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of tissue harvesting, mincing, and transport devices described above may be actuated electromechanically, e.g., using one or more electrical motors, solenoids, etc. However, other actuation modes may be suitable as well, e.g., pneumatically, and/or hydraulically. Various suitable ways in which such alternative forms of actuation may be provided in a device as described above will be apparent to those of ordinary skill in the art in view of the teachings herein.

Versions of tissue harvesting, mincing, and transport devices described above may have various types of construction. By way of example only, any of the devices described herein, or components thereof, may be constructed from suitable metals, ceramics, plastics, or combinations thereof. Furthermore, although not required, the construction of devices described herein may be adapted to be compatible with or optimize their use with various imaging technologies. For instance, a device adapted for use with MRI may be constructed from all non-ferromagnetic materials. Also for instance, when using optional imaging technologies with devices described herein, certain adaptations may include modifications to materials of construction such that portions or the device may readily appear in a resultant image. For instance, it may be desirable to have the side aperture of the needle appear visible in an image to confirm placement of the device before harvesting a tissue specimen. Based on the teachings herein, these and other modifications to the construction of devices described herein will be apparent to those of ordinary skill in the art.

Versions of tissue harvesting, mincing, and transport devices described above may have application in conventional medical treatments and procedures conducted by a medical professional, as well as application in robotic-assisted medical treatments and procedures.

Versions of tissue harvesting, mincing, and transport devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A device for obtaining and preparing biological components for use in a medical application, the device comprising:
    (a) a cannula having a side aperture configured to receive a tissue specimen;
    (b) a divider located within the cannula, wherein the divider and the cannula define a first lumen and second lumen, wherein the divider has a first plurality of apertures, wherein the first plurality of apertures provide passages from the first lumen to the second lumen;
    (c) a cutter, wherein the cutter is positionable within the first lumen of the cannula, wherein the cutter is operably configured to translate within the first lumen, wherein the cutter is operably configured to sever the tissue specimen received within the side aperture of the cannula, wherein the cutter includes a second plurality of apertures operably configured to selectively open and close the passages from the first lumen to the second lumen; and
    (d) a plunger, wherein the plunger is positionable within the cutter, wherein the plunger is operably configured to translate within the cutter, wherein the plunger is operably configured to urge the tissue specimen severed by the cutter into the passages, wherein the plunger comprises a tube having a closed distal end and a side opening proximal to the closed distal end, wherein the plunger is configured to receive and transport a fluid from a fluid source to the passages defined by the first plurality of apertures of the divider via the side opening.

2. The device of claim 1, wherein the cutter is operably configured to rotate.

3. The device of claim 1 further comprising a piercing tip at a distal end of the cannula, wherein the divider is associated with the piercing tip and extends proximally within the cannula.

4. The device of claim 1, further comprising:
    (a) a lead screw in communication with the cutter and the plunger, wherein the lead screw comprises a threaded portion and is operably configured to rotate;
    (b) a first threaded member, wherein the first threaded member is operably configured to translate along the lead screw, wherein the first threaded member is in communication with the cutter and is operably configured to translate the cutter; and
    (c) a second threaded member, wherein the second threaded member is operably configured to translate along the lead screw, wherein the second threaded member is in communication with the plunger and is operably configured to translate the plunger.

5. The device of claim 4, wherein the cutter is operably configured to rotate, wherein the first threaded member is operably configured to permit the cutter to rotate as the cutter translates.

6. The device of claim 5, wherein the lead screw comprises a free-wheeling portion, wherein the first threaded member is operable to cease translation while the lead screw rotates upon the first threaded member reaching the free-wheeling portion, wherein the cutter is operably configured to rotate as the first threaded member is located at the free-wheeling portion.

7. The device of claim 5, wherein the lead screw comprises a first threaded portion and a second threaded portion, wherein the first threaded portion comprises a fine pitch threading, and wherein the second threaded portion comprises a coarse pitch threading.

8. The device of claim 7, wherein the first threaded portion is positioned along a proximal portion of the lead screw, and wherein the second threaded portion is positioned along a distal portion of the lead screw.

9. The device of claim 8, wherein the first and second threaded members are configured to rotate at a first rotational speed while the lead screw rotates at a second rotational speed.

* * * * *